(12) United States Patent
Nagaoka et al.

(10) Patent No.: US 7,003,071 B2
(45) Date of Patent: Feb. 21, 2006

(54) X-RAY CT APPARATUS, X-RAY CT APPARATUS AFTERGLOW CORRECTION METHOD, AND AFTERGLOW CORRECTION PROGRAM

(75) Inventors: Takayuki Nagaoka, Chiba (JP); Osamu Miyazaki, Ibaraki (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 10/488,153

(22) PCT Filed: Aug. 29, 2002

(86) PCT No.: PCT/JP02/08706

§ 371 (c)(1), (2), (4) Date: Sep. 20, 2004

(87) PCT Pub. No.: WO03/017842

PCT Pub. Date: Mar. 6, 2003

(65) Prior Publication Data

US 2005/0036582 A1    Feb. 17, 2005

(30) Foreign Application Priority Data

Aug. 30, 2001   (JP) ............................. 2001-261792

(51) Int. Cl.
*A61B 6/03* (2006.01)

(52) U.S. Cl. ............................. 378/19; 378/8; 378/901

(58) Field of Classification Search .................... 378/4, 378/8, 15, 19, 901

See application file for complete search history.

(56) References Cited

U.S. PATENT DOCUMENTS 5,249,123 A * 9/1993 Hsieh .......................... 378/19
5,359,638 A * 10/1994 Hsieh et al. .................... 378/4
6,295,331 B1 * 9/2001 Hsieh ........................... 378/19
6,493,646 B1 * 12/2002 Hsieh et al. ................. 702/104

FOREIGN PATENT DOCUMENTS

JP    62-14044    1/1987
JP    06-90945    4/1994

OTHER PUBLICATIONS

Kenjiro Oda, Yoshio Matsumoto, Shin-ichiro Mishima, "Optimizing Power of Genetic Algorithm Concerning Parameter Estimation of Mathematical Model: Application To An Organic Material Decomposition Model", 1996, (and English translation of section 4).

* cited by examiner

*Primary Examiner*—David V Bruce
(74) *Attorney, Agent, or Firm*—Cooper & Dunham LLP (57) ABSTRACT

An X-ray CT apparatus including an X-ray source for applying X-rays to an object, an X-ray detector arranged to face the X-ray source for determining the amount of transmitted X-rays of the object as projection data, basic-data acquisition means for acquiring response data of the projection data as basic data with no object present in advance every time the image of the object is acquired, analyzing means for analyzing an afterglow component of the acquired basic data into a plurality of time constants and their component ratios, storage means for storing the analyzed time constants and component ratios, correcting means for extracting an afterglow component of the projection data on the basis of the stored time constants and component ratios during radiography of the object and removing the extracted afterglow component of the projection data from the projection data to produce corrected projection data, reconstructing means for reconstructing an image using the produced corrected projection data, and display means for displaying the reconstructed image.

17 Claims, 8 Drawing Sheets

X-RAY CT APPARATUS, X-RAY CT APPARATUS AFTERGLOW CORRECTION METHOD, AND AFTERGLOW CORRECTION PROGRAM

TECHNICAL FIELD

The present invention relates to an X-ray CT apparatus and a method and a program for correcting the afterglow of the same.

BACKGROUND ART

A solid-state type X-ray detector of X-ray CT apparatus is becoming dominant. Since the sensitivity of the X-ray detector has improved, effects of after-images resulting from an afterglow of scintillators have become notable, thus decreasing the time resolution and the quality of pictures. Specifically, such X-ray detectors include scintillators that generate fluorescent when receiving X-rays, detecting the X-rays by detecting the fluorescent with photodetecting means such as a photodiode. The fluorescent of the scintillators, however, does not stop immediately even after termination of the X-ray irradiation, to attenuate together with a delay in response, causing afterglow. Such afterglow is mixed in projection data to be sampled, causing after-images (artifact). Several methods are presented to correct the afterglow causing the after-images.

One of the methods is a method of correcting the shortest time-constant component at any time (refer to Japanese Examined Patent Publication No. 7-090024). Another method is a correction method using linear transformation of detector output (refer to Japanese Examined Patent Publication No. 7-102211). Another method is a correction method in correspondence with plural time constants at any time (refer to Japanese Unexamined Patent Publication No. 6-90945). Another method is a correction method using convolution integration (refer to Japanese Unexamined Patent Publication No. 6-343629).

The method disclosed in Japanese Unexamined Patent Publication No. 6-90945 is to acquire the time constant of the longest impulse response time and its component using a device including a radiation detector having an exponential impulse response determined by plural different time constants, and after eliminating the component, to acquire the next longest time constant and its component ratio and eliminate the component, wherein the process is repeated until influence of afterglow components is lost. It is described that the data of the time constants and their components are obtained in a factory by operating a CT apparatus with no object of tomogram present in an imaging opening. In other words, the impulse response data is collected only before shipping products from a factory.

However, since the characteristics of the X-ray detector of detecting afterglow and so on vary depending on environments including temperature during photographing of an object and secular change, the aforesaid methods are possibly unable to sufficiently eliminate afterglow components.

Such X-ray CT apparatus are required to accurately extract and eliminate afterglow components contained in projection data for further reducing effects of afterglow.

DISCLOSURE OF INVENTION

An object of the present invention is to reduce the influence of afterglow in an X-ray CT apparatus.

According to the present invention, an X-ray CT apparatus comprising an X-ray source for irradiating X-rays to an object and an X-ray detector arranged to face the X-ray source and detecting the amount of transmitted X-rays of the object as projection data. Further comprising, to solve above-described problems, basic-data acquisition means for acquiring response data of the projection data as basic data with no object present every time before the image of the object is acquired, analyzing means for breaking down an afterglow component of the acquired basic data into a plurality of time constants and their component ratios, storage means for storing the broken-down time constants and component ratios, correcting means for extracting an afterglow component of the projection data on the basis of the stored time constants and component ratios during radiography of the object and eliminating the extracted afterglow component of the projection data from the projection data to produce corrected projection data, reconstructing means for reconstructing an image using the produced corrected projection data, and display means for displaying the reconstructed image.

The above-described problems, also, are solved by a method or a program for correcting afterglow of an X-ray CT apparatus having an X-ray source for applying X-rays to an object and an X-ray detector arranged to face the X-ray source for detecting the amount of transmitted X-rays of the object as projection data. The method or the program comprises, a basic-data acquisition step of acquiring response data of the projection data with no object as basic data every time before the image of the object is acquired, an analyzing step for breaking down an afterglow component of the acquired basic data into a plurality of time constants and their component ratios, a storing step of memorizing the analyzed time constants and component ratios, a correcting step of extracting an afterglow component of the projection data on the basis of the stored time constants and component ratios during radiography of the object and removing the extracted afterglow component of the projection data from the projection data to produce corrected projection data, a reconstructing step of reconstructing an image using the produced corrected projection data, and a displaying step of displaying the reconstructed image.

According to the present invention, since an afterglow component is broken-down into a plurality of time constants and their component ratios on the basis of the basic data every time the image of the object is acquired, the component ratio for the time constants can be accurately determined, so that an afterglow signal component is accurately calculated. Since corrected projection data in which an afterglow component is eliminated from the projection data are acquired by using the accurate component ratio for the time components, the effects of afterglow can be further reduced, whereby the occurrence of artifact is reduced and the time resolution of the X-ray CT apparatus is improved.

The time constants and their component ratio of the previously acquired corrected projection data may be memorized in the storage means and may be used when new corrected projection data are sequentially acquired.

With such an arrangement, the time constants and their component ratio of the latest corrected projection data are used for new corrected projection data to be acquired the next time. Therefore, since for example, the amount of X-rays for the object in the slice position adjacent to the previous CT image is substantially the same as that of the previous one, the afterglow components caused thereby are also substantially the same. In such a case, since there is no need to store previous data accumulatively, the memory capacity used in the correcting means can be reduced.

An X-ray CT apparatus may comprise, an X-ray source for irradiating X-rays to an object, an X-ray detector arranged to face the X-ray source for detecting the amount of transmitted X-rays through the object as projection data, actual-measurement acquisition means for acquiring the projection data of a step response, as an actual measurement, when continuous X-rays are irradiated to the X-ray detector with no object present and thereafter the irradiation is stopped; analyzing means for breaking down the step response of the acquired actual measurement into an impulse response, representing the calculation of the step response through the convolution integration of the analyzed impulse response, and calculating a plurality of time constants and their component ratios asymptotically and recursively that make the error between the actual measurement and the calculation lower than a set value, storage means for storing the calculated time constants and component ratios, correcting means for eliminating an afterglow component of the stored projection data from the projection data to produce corrected projection data during radiography of the object, reconstructing means for reconstructing an image using the produced corrected projection data, and display means for displaying the reconstructed image.

Accordingly, the component ratios for the time constants are obtained by repeating the recursive operation until the error becomes a set value or less. Accordingly, the accuracy of the time constants and their component ratios is ensured, allowing high-reliability afterglow correction.

An X-ray CT apparatus may comprise, an X-ray source for applying X-rays to an object, an X-ray detector arranged to face the X-ray source for detecting the amount of transmitted X-rays through the object as projection data, basic-data acquisition means for acquiring response data of the projection data as basic data in advance with no object present, analyzing means for analyzing an afterglow component of the acquired basic data into a plurality of time constants and their component ratios by using a genetic algorithm, storage means for storing the analyzed time constants and component ratios, correcting means for extracting an afterglow component of the projection data on the basis of the stored time constants and component ratios during radiography of the object and eliminating the extracted afterglow component of the projection data from the projection data to produce corrected projection data, reconstructing means for reconstructing an image using the produced corrected projection data, and display means for displaying the reconstructed image.

Accordingly, the use of the genetic algorithm when determining the component ratios for the time constants by a recursive operation accelerates the convergence of the recursive operation, thus providing accurate component ratios at an early stage.

The acquisition of the basic data in the response characteristic, the calculation of the component ratios for the time constants, and the correction of the projection data may be performed for each channel for the X-ray detectors having multiple channels, for example, approximately one thousand channels.

For an X-ray detector providing multiple modules having a detecting section corresponding to multiple channels made of the same element, the acquisition of the basic data and the calculation of the component ratios for the time constants may be performed only for part of the channels representing each module, while common correction may be made for the projection data corresponding to the modules. Specifically, since the channels made of the same element have a similar response characteristic, the time required for calculation of the component ratios for the time constants is reduced by correcting each channel on the basis of the basic data of a representative channel, and the capacity of a memory for storing them can also be reduced. For example, in an X-ray detector having an X-ray detecting section for 16 channels as one module, the basic data may be acquired only for one or more partial channels of each module.

BEST MODE FOR CARRYING OUT THE INVENTION

Referring to the drawings, embodiments of an X-ray CT apparatus incorporating the present invention will be specifically described.

According to the embodiments of the invention, an X-ray tube is used as an X-ray source. In this specification, afterglow is the output (projection data) of an X-ray detector, while an after-image is given as an image after the afterglow has been reconstructed.

(First Embodiment)

Figure 1:
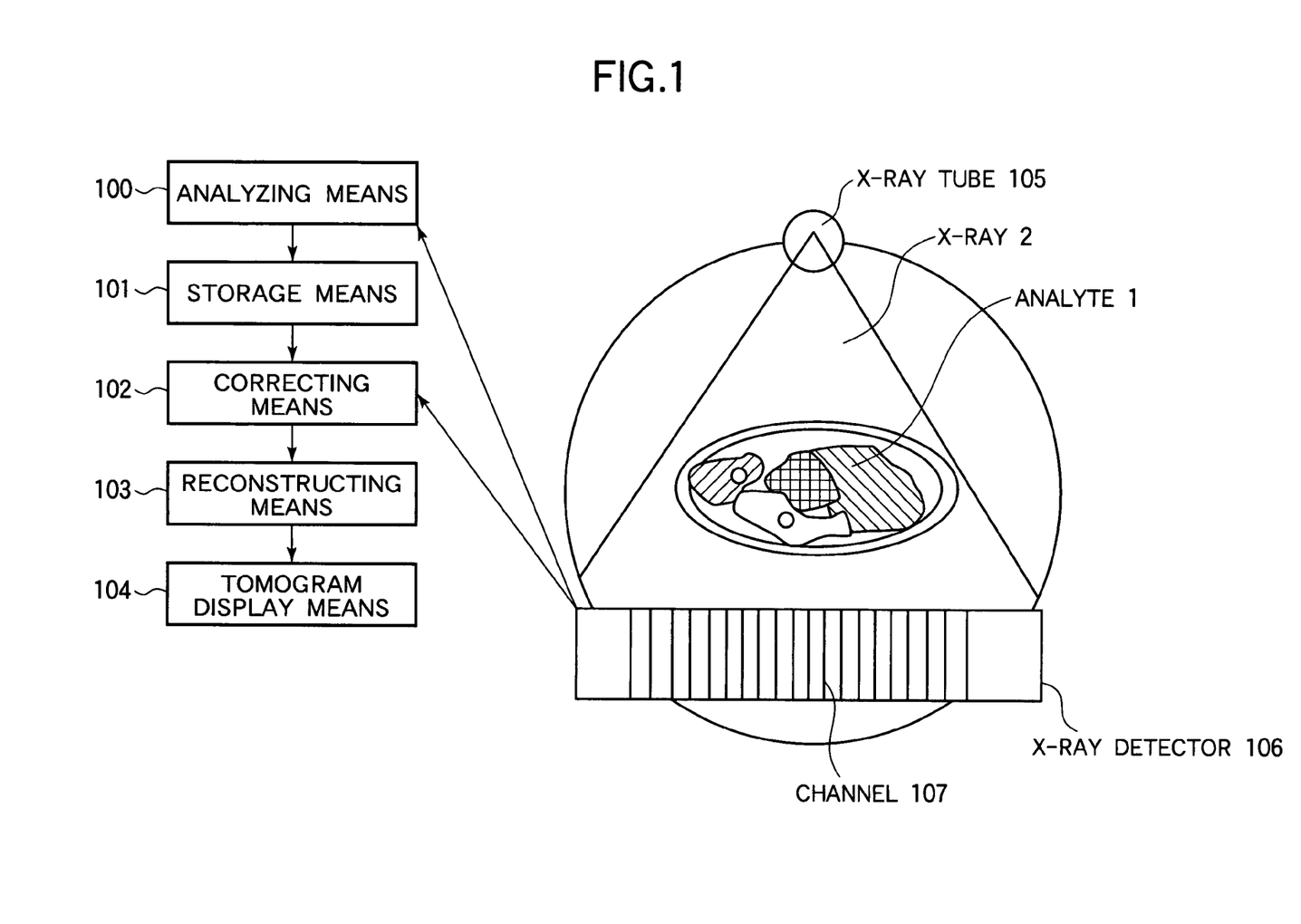
FIG. 1 is an explanatory diagram of an X-ray CT apparatus including a correcting means for removing afterglow, according to the embodiment of the present invention.

Referring to FIG. 1, the basic structure of the X-ray CT apparatus is as follows. X-rays 2 are applied from an X-ray tube 105 to capture projection data representing the amount of attenuation of the X-rays 2 that have passed through an object 1 and taken in an X-ray detector 106 arranged to face the X-ray tube 105 interposing the object 1 therebetween and having multiple channels 107.

An image is reconstructed with a reconstructing means 103 basis on the projection data and displayed with a tomogram display means 104.

Basic data about the response characteristic of the projection data are acquired for every channel 107 under a state that object 1 does not exist. The apparatus comprises an analyzing means 100 for breaking down the basic data for every channel 107 and decomposing the response characteristic into components for every time-constant, a storage means 101 for memorizing the component ratio of time constants, and a correcting means 102 for converting the projection data to corrected projection data in which the effects of the after-image are removed during radiography of the object 1.

Figure 2:
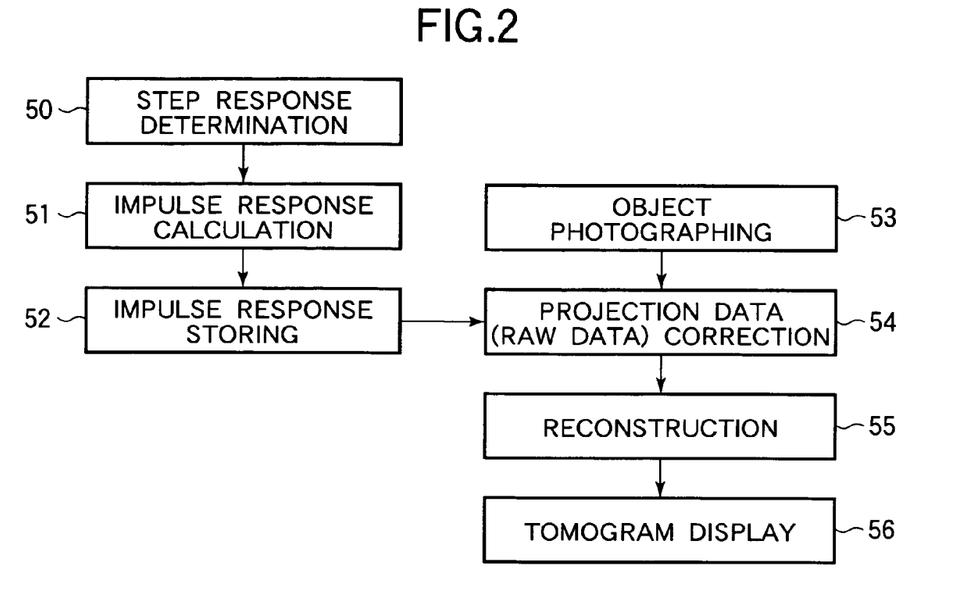
FIG. 2 is a flowchart for explaining the operation of the X-ray CT apparatus shown in FIG. 1.

Referring next to FIG. 2, a method for correcting the after-image in the X-ray CT apparatus of FIG. 1 will be described.

The determination of a step response (Step 50) and the calculation of an impulse response (Step 51), shown in FIG. 2, are carried out by the analyzing means 100. The correction of the projection data (raw data) (Step 54) is carried out by the correcting means 102. The storage of the impulse response (Step 52) is carried out by the storage means 101.

The step response is measured with no object 1 present and thus obtained projection data are used as basic data (Step 50).

Figure 3A:
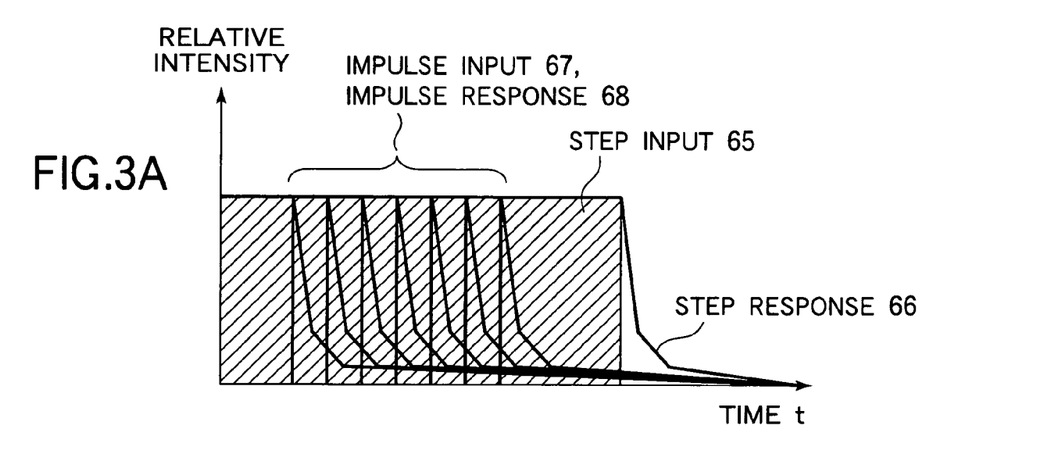
FIG. 3 is an explanatory diagram of a method for determining impulse response by the measurement of step response, shown in the flowchart of FIG. 2.
Figure 3B:
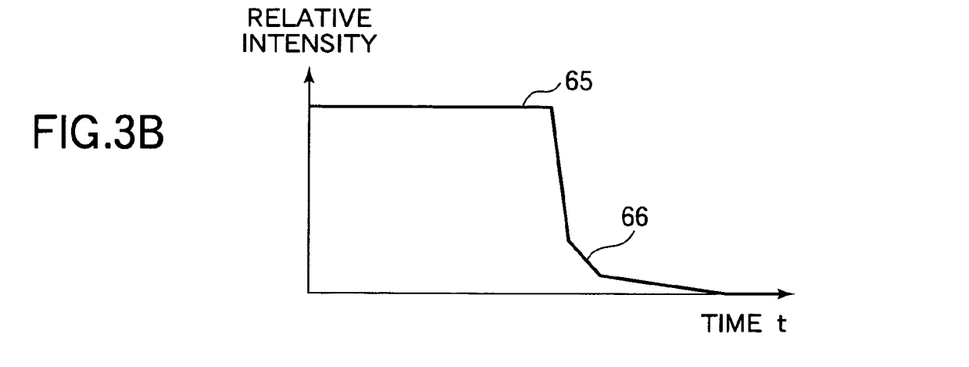
Figure 3C:
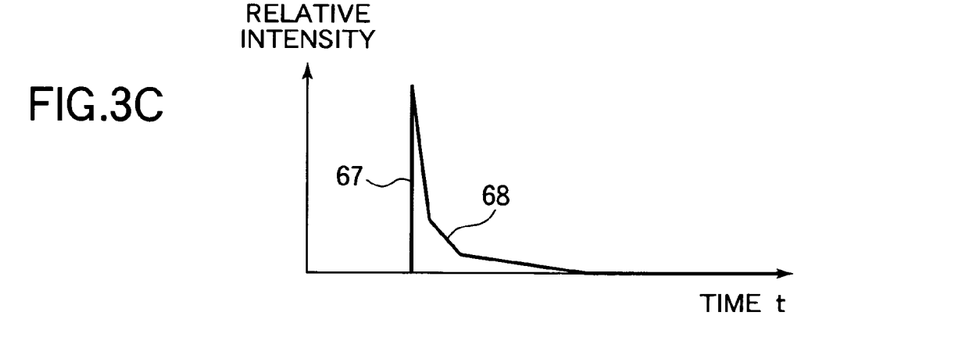

The correcting means has a stop means for shutting off the output of X-rays at a predetermined arbitrary sampling number or time. The stop means stops the output from the X-ray tube 105, shown in FIG. 1, at any time, e.g., at the point in time when the half of scanning time has passed after the X-ray CT apparatus has emitted the X-rays. From the data of determination of the step response thus obtained (Step 50), the component ratios for the time constants regarding the impulse response 68, shown in FIG. 3, is analyzed to calculate the impulse response (Step 51). The component ratio of the time constants of the impulse response 68 is stored for every channel (Step 52).

When the object is actually subjected to radiography (Step 53), as shown in FIG. 2, projection data are taken from the X-ray detector 106 of FIG. 1 during scanning. The projection data are corrected every time they are taken in (Step 54).

The corrected projection data are reconstructed as in general X-ray CT apparatus (Step 55) to construct the tomogram of the object 1. The tomogram is displayed on a tomogram display means 104 (Step 56).

A method for calculating the impulse response from the determination of the step response shown in FIG. 2 will be described.

As referred to FIG. 3, a step response 66 serving as the base of the correction is radiographed and acquired as basic data with no object 1 present.

The application of X-rays for obtaining the step response 66 and the response of the X-ray detector 106, shown in FIG. 1, are as follows.

A step input 65 is the same as continuous impulse inputs 67, as shown in FIG. 3(*a*). Since the impulse response 68 is the result of output on the assumption that ideal impulses were inputted, as shown in FIG. 3(*c*). Since the step response 66 is an output from continuous inputs, the step response 66 can be expressed as a convolution integral of the impulse response 68. Conversely, if the impulse response 68 can be calculated, the step response 66 is determined.

Since the ON/OFF control of the X-ray tube 105, shown in FIG. 1, is difficult, it is difficult to obtain the impulse response 68 shown in FIG. 3(*c*) as compared with the step response 66 shown in FIG. 3(*b*).

Specifically, since the pulse width of the step input 65 is longer than that of the impulse input 67, the control becomes easy and the step response 66 can be determined more easily.

The impulse response 68 has an exponential characteristic having a component ratio of multiple time constants, as expressed in the following equation $$X(t) = \Sigma Si \cdot \exp(-t/\tau i) \qquad (1),$$

where $X(t)$ is the impulse response, t designates the time from impulse input, $Si (i=1, 2, \ldots n)$ does the component ratio of time constants, and $\tau i$ does different time constants as many as n. Symbol i denotes a natural number assigned to the respective time constants. Thus, when a set of the component ratio $Si$ of time constants and the n different time constants is determined, the impulse response 68 can be reproduced. Further, the step response 66 can be reproduced by convolution integration thereof.

As one of methods of determining the set of the component ratio $Si$ of the time constants and the n different time constants $\tau i$, the n different time constants $\tau i$ are predetermined in geometric progression or logarithmically in advance. The distribution of the component ratio $Si$ corresponding to the time constants is estimated and assumed temporarily on the basis of an empirical value or the like.

A method for finding the calculation of the impulse response 68 from the step response 66 shown in FIG. 3 will now be described.

The relationship between the step response 66 in FIG. 3(*b*) and the impulse response 68 in FIG. 3(*c*) is expressed as convolution integral, as in the equation $$Z(t) = \sum_{i=0}^{t} \times (t-i)(t > t_0), \qquad (2)$$

where $Z(t)$: actual measurement of the step response when the time t has exceeded $t_0$; and $X(t-i)$: the impulse response at time t and with time-constant component ratio i.

Figure 4:
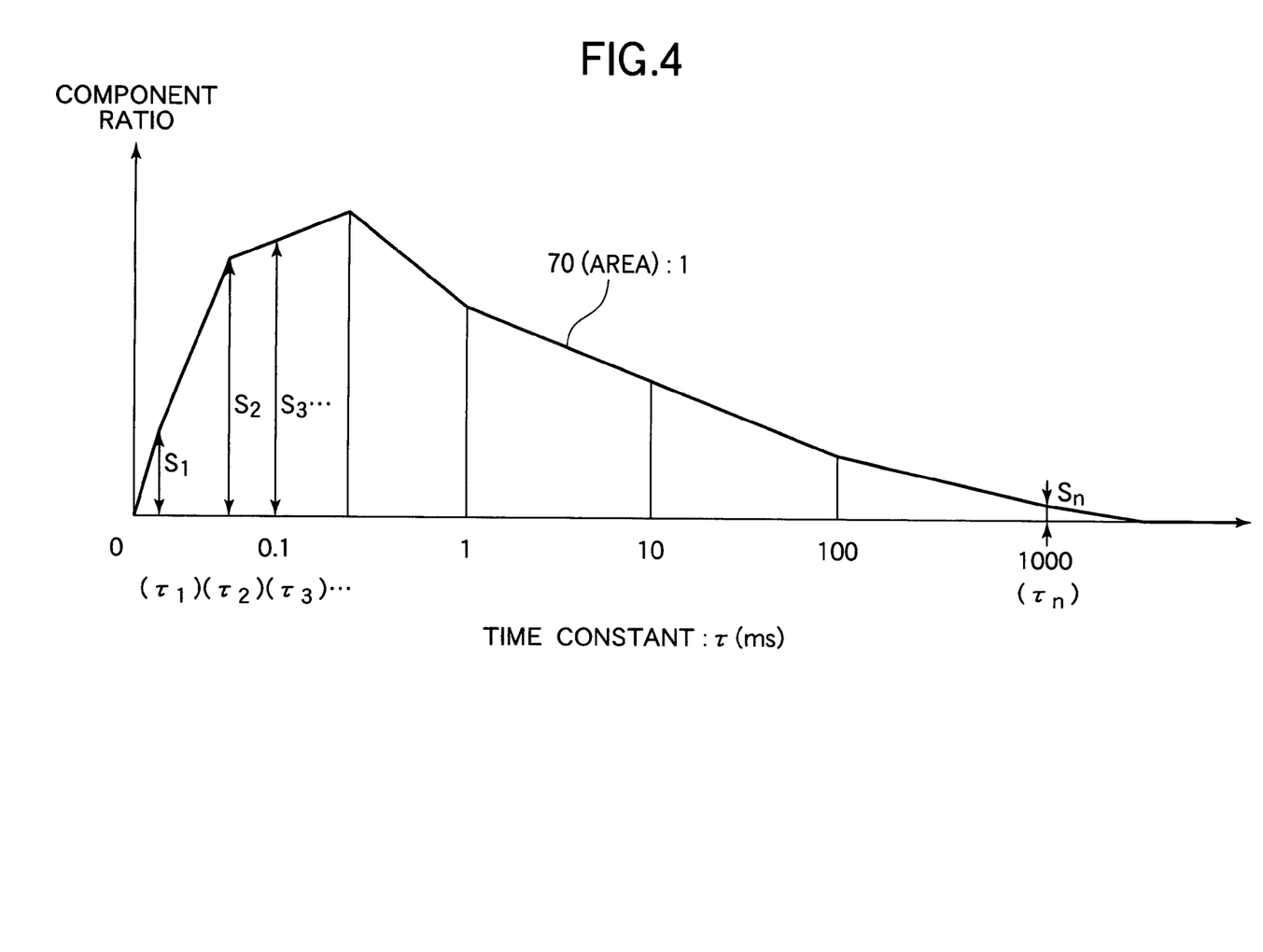
FIG. 4 is an explanatory diagram of a method for determining an impulse response from a component ratio of time constants, shown in the flowchart of FIG. 2.

When the time constant is allotted to abscissa and the component ratio is allotted to ordinate, the distribution 70 of the component ratios $Si$ of the time constants is as shown in FIG. 4, wherein the integral is 1. The distribution 70 of the component ratio $Si$ of the time constants has dose correlations respectively with the impulse response 68 and the step response 66 shown in FIG. 3. Therefore, when the distribution 70 of the component ratio $Si$ of the time constants related to the impulse response is determined, the impulse response 68 and the step response 66, shown in FIG. 3, can be determined. As shown in FIG. 4, a plurality of component ratios $Si$ are, for example, of the time constants of from 0.1 ms to 1,000 ms.

Figure 5:
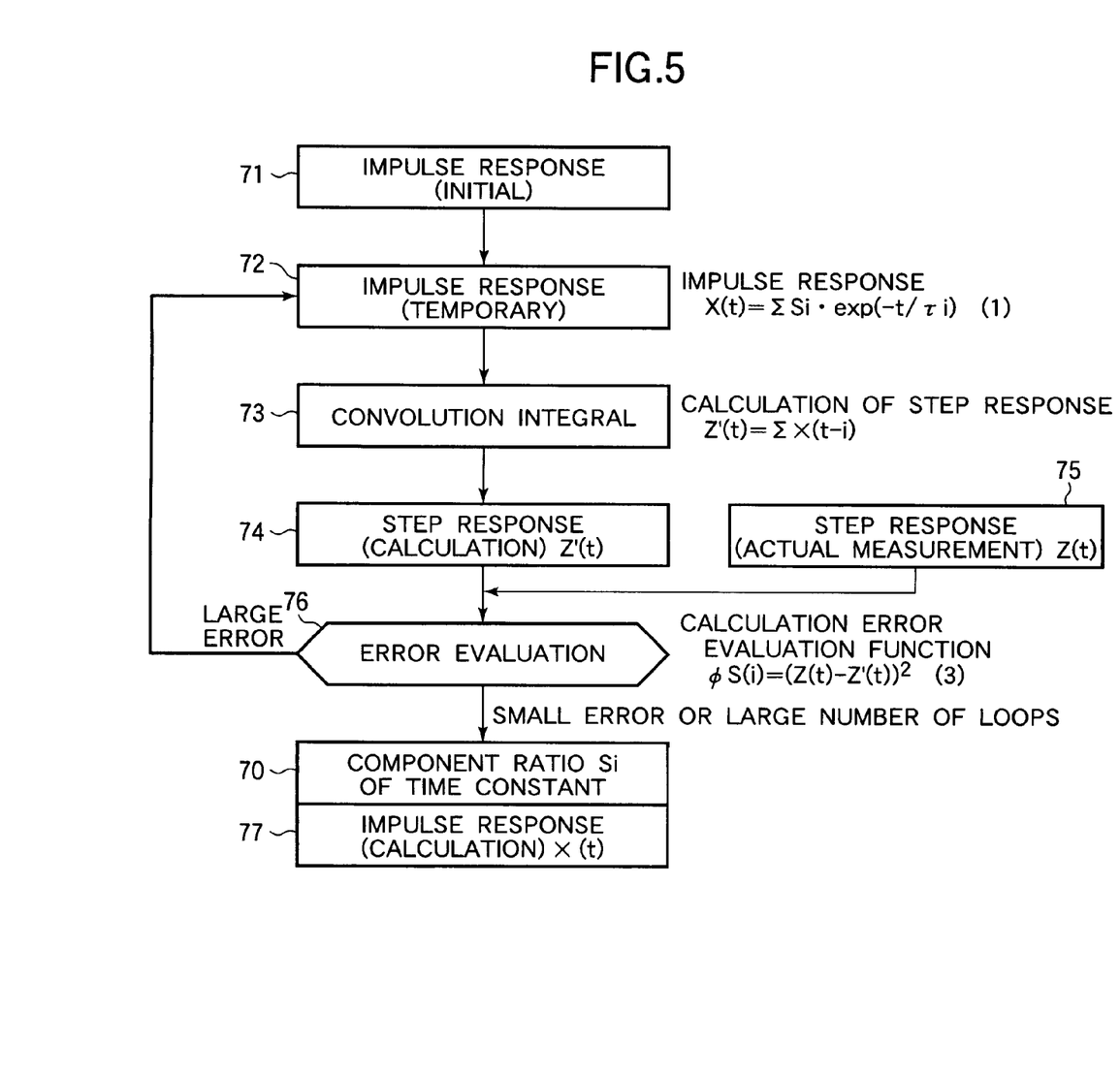
FIG. 5 is an explanatory diagram of a correcting method shown in FIG. 2 and a method for determining the component ratio of the time constants, necessary to determine the impulse response shown in FIGS. 3 and 4.

Referring to the flowchart of FIG. 5, a method for finding the distribution 70 of the component ratios $Si$ of the time constants and the calculated value $X(t)$ of the impulse response from the actual measurement $Z(t)$ of actually measured step response will be described.

The plurality of time constants and the initial values of the respective component ratios of the time constants related to the impulse response are arbitrarily set (Step 71). A temporary value of the impulse response $X(t)$ is found by calculation of Equation (1) (Step 72). The calculation $Z'(t)$ of the step response is found (Step 74) by convolution integration of Equation (2) (Step 73). The square error between the calculation $Z'(t)$ of the step response and the actual measurement $Z(t)$ of the step response (Step 75) is set as evaluation function $\phi(Si)$, as in the following equation $$\phi(Si) = (Z(t) - Z'(t))^2 \qquad (3)$$

The impulse response is recalculated using the equation (1) depending on the magnitude of evaluation function $\phi(Si)$ while the set of the component ratios $Si$ of the time constants is changed in accordance with, for example, random numbers little by little by using a feedback loop for correcting the distribution 70 of the component ratios Si of the time constants shown in FIG. 4. Then the error between the calculation Z'(t) of the step response and the actual measurement Z(t) of the step response is evaluated using the equation (3) (Step 76).

Although the evaluation function $\phi(Si)$ is asymptotically decreased as described above, in general, the evaluation function $\phi(Si)$ cannot always be reduced to zero. Thus, the distribution 70 of the component ratios Si of the time constants shown in FIG. 4, which reproduces the step response 66 of FIG. 3, is determined by setting a threshold of the evaluation function $\phi(Si)$ becomes sufficiently practically low and enabling escape from the feedback loop when the evaluation function $\phi(Si)$ becomes the threshold or less(Step 70). The calculation X(t) of the impulse response is determined by the equation (1) on the basis of the distribution 70 of the component ratios Si of the time constants (Step 77).

The method of acquiring corrected projection data by correcting the projection data (measurement data) will then be described.

Figure 6:
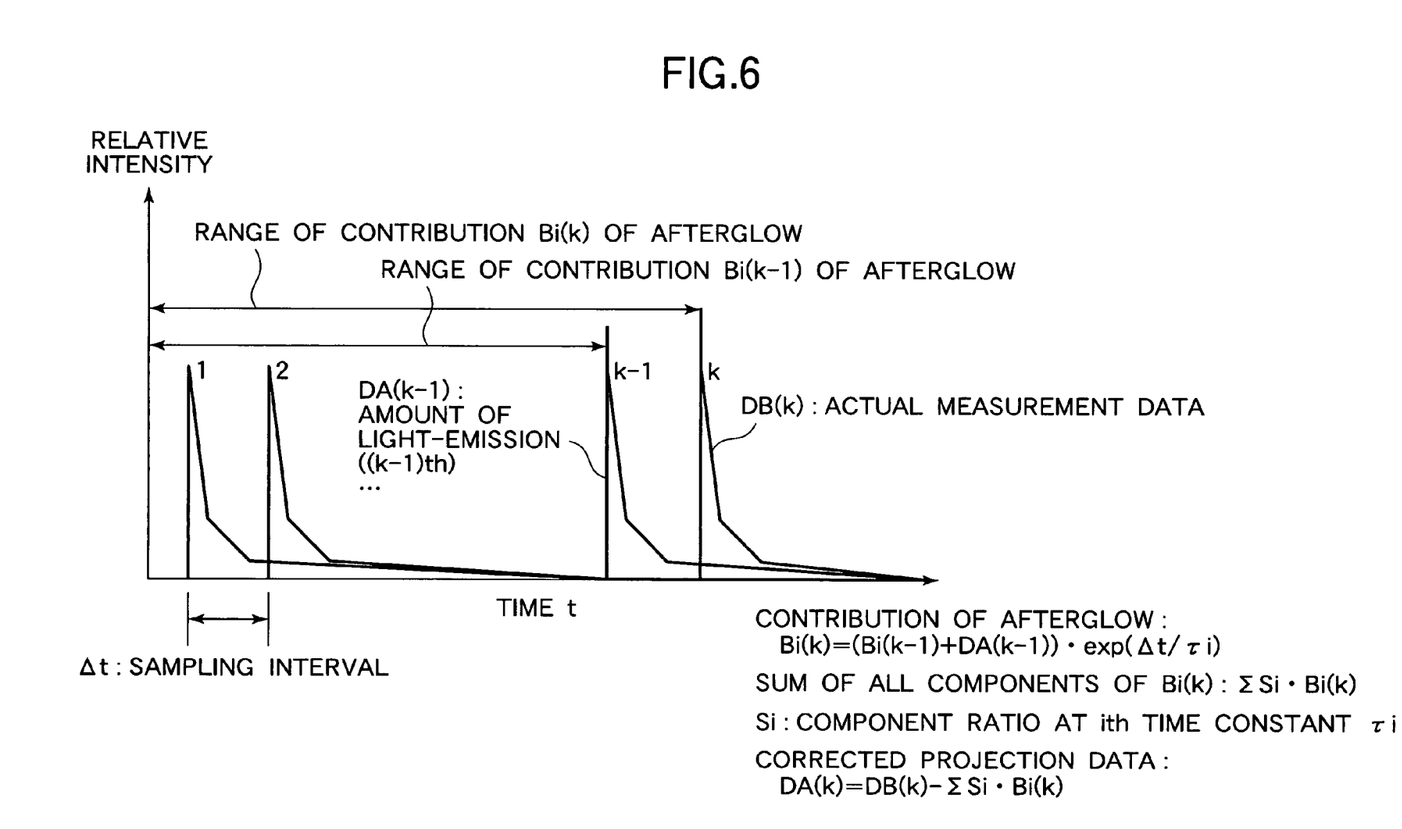
FIG. 6 is an explanatory diagram of an algorithm for eliminating afterglow.

Referring to FIG. 6, the measurement data concerning afterglow and the amount of luminescence can be expressed by allotting time to abscissa and the intensity of luminescence to ordinate.

Corrected projection data DA(k) for the k-th sampling number can be given by the equation $$DA(k) = DB(k) - \sum_{i=0}^{n} Si \cdot Bi(k) \quad (4)$$

where

DA(k): corrected projection data of the k-th sampling number, where DA(0)=DB(0);

DB(k): measurement data of the k-th sampling number;

Si: the ratio of components for the i-th time constant; and

Bi(k): contribution of afterglow of the k-th sampling number and the i-th time constant, wherein Bi(0)=0.

Specifically, as expressed by the equation (4), Bi(k) is the contributory part of the afterglow for every component ratio of the i-th time constant. When the sum of all contributory parts Bi(k) of the afterglow for every component ratio of the i-th time constants is subtracted from the present projection data DB(k), the corrected projection data DA(k) is obtainable.

The calculation of the corrected projection data can be achieved with a recursive filter.

The corrected projection data DA(k) is calculated for every channel 107 of the X-ray detector 106 shown in FIG. 1.

The contributory parts Bi(k) of the afterglow for every component ratio of the time constants at the time can be calculated by the following equation with respect to the range shown in FIG. 6.

$$Bi(k)=(Bi(k-1)+DA(k-1)\cdot\exp(-\Delta t/\tau i) \quad (5),$$

where

Bi(k-1): contribution of the afterglow for every component ratio of the time constants of the (k-1)th sampling number immediately before the k-th sampling number;

DA(k-1): corrected projection data of the (k-1)th sampling number immediately before the k-th sampling number;

$\Delta t$: time interval between the k-th sampling number and the (k-1)th sampling number immediately therebefore; and $\tau i$: i-th time constant ($\tau 0=0.1$ ms, . . . $\tau 4=1,000$ ms).

Specifically, as expressed by the equation (5), the contributory parts Bi(k) of the afterglow for every component ratio of time constants at the k-th sampling number is found by multiplying the sum of the contributory part Bi(k-1) of the afterglow for time constant $\tau i$ at the (k-1)th sampling number immediately before the k-th sampling number and corrected projection data DA(k-1) at the (k-1)the sampling number immediately before the k-th sampling number by the attenuation $\exp(-\Delta t/\tau i)$ of $\Delta t$ corresponding to the time constant $\Delta i$.

The calculations by the equations (4) and (5) are performed for every channel 107 of the X-ray detector 106 shown in FIG. 1, to convent into the corrected projection data DA(k).

The corrected projection data DA(k) is stored in the storage means 101 shown in FIG. 1 for every channel 107 and every component ratio of the time constants to update the result at every calculation.

An image after correction is formed using the corrected projection data DA(k) with the reconstructing means 103, shown in FIG. 1.

According to the embodiment, as described above, because the time constants that indicate afterglow components are determined on the basis of the basic data acquired with no object present; thus, the component ratios for the time constants can be accurately obtained, allowing accurate calculation of the afterglow component. Since corrected projection data is acquired by using the accurate component ratios for the time constants, the effects of afterglow can be decreased, thus reducing the occurrence of artifacts to improve the time resolution of devices.

With the correcting means, new corrected projection data is acquired, for every sampling time, by subtracting the sum of the values found by multiplying the value obtained by breaking down the previously acquired corrected projection data depending on the component ratios for the time constants and the value of the afterglow component for every time constants by the time of sampling multiple times before at the calculation of the corrected projection data by the respective attenuations of the time constants from the projection data at the sampling time for the correction object. Accordingly, if the respective afterglow components of the time constants at the sampling time when the corrected projection data is previously calculated and the corrected projection data at that time are found, corrected projection data at the latest sampling time can be acquired. Therefore, there is no need to accumulate the preceding data for storage, decreasing necessary memory capacity.

Since a recursive operation is done until the error between the calculation of a step response represented by convolution integration of the impulse response obtained by using the component ratios for the time constants that are calculated on the basis of the basic data and the actual measurement of the step response obtained as the basic data becomes a predetermined threshold or less, the accuracy of the component ratios for the time constants is ensured, thus allow high-reliability afterglow correction.

(Second Embodiment)

Figure 7:
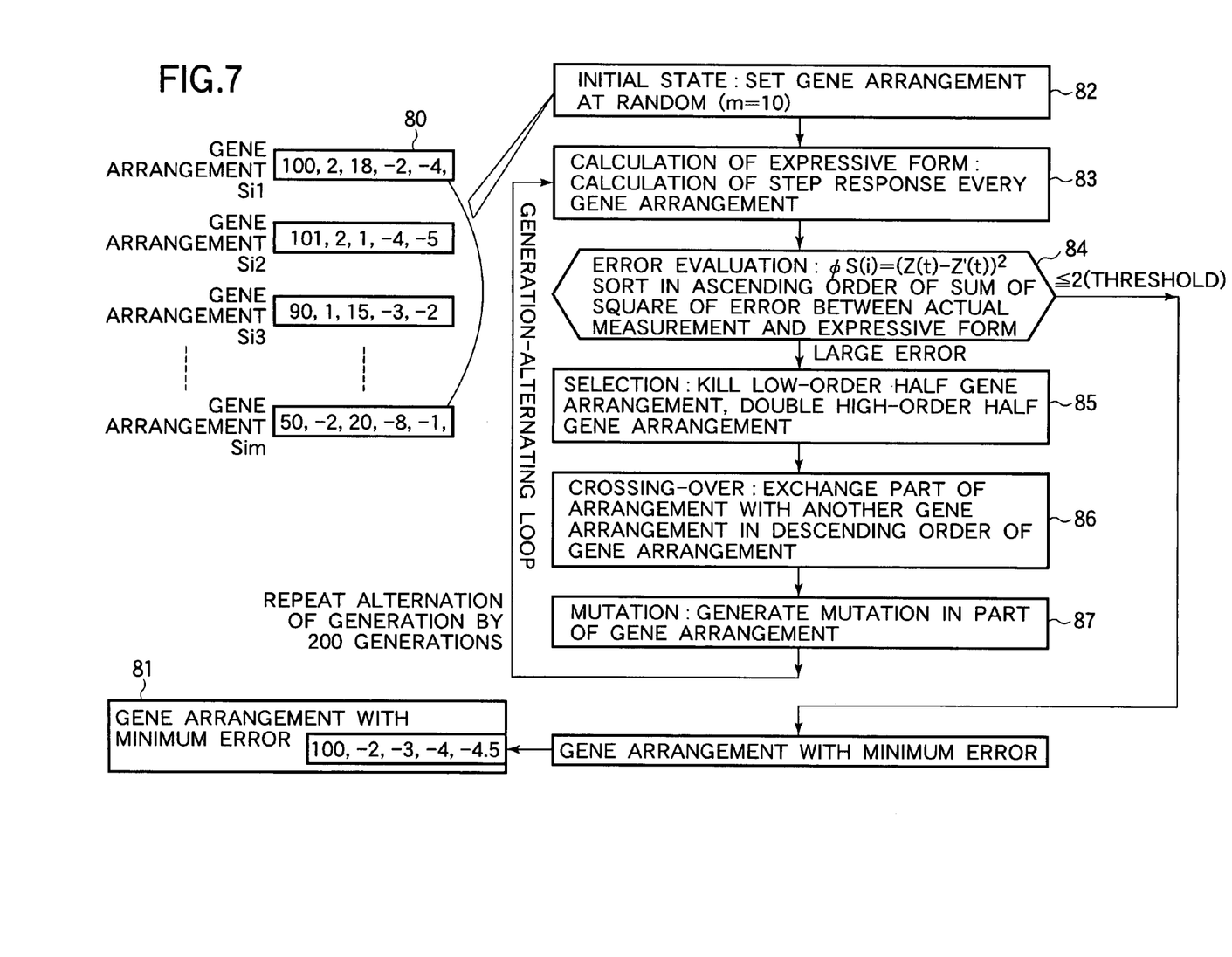
FIG. 7 is an explanatory diagram of a method for finding a component ratio for time constants using genetic algorithm to determine a calculation value of an impulse response for the same purpose as that of FIG. 5.

A second embodiment of the X-ray CT apparatus incorporating the invention will be described. The description of the same parts as those of the first embodiment will be omitted and only differences will be described. The embodiment is characterized in that a genetic algorithm is applied to calculate the component ratio of the time constants for the impulse response on the basis of the basic data about the step response obtained with no object present. The flowchart of FIG. 7 shows an example of the application of a genetic algorithm as analyzing means for the impulse response 68 and the step response 66 for finding the calculation of the impulse response 68 in FIG. 3. The genetic algorithm is one of general methods for optimization.

Figure 8:
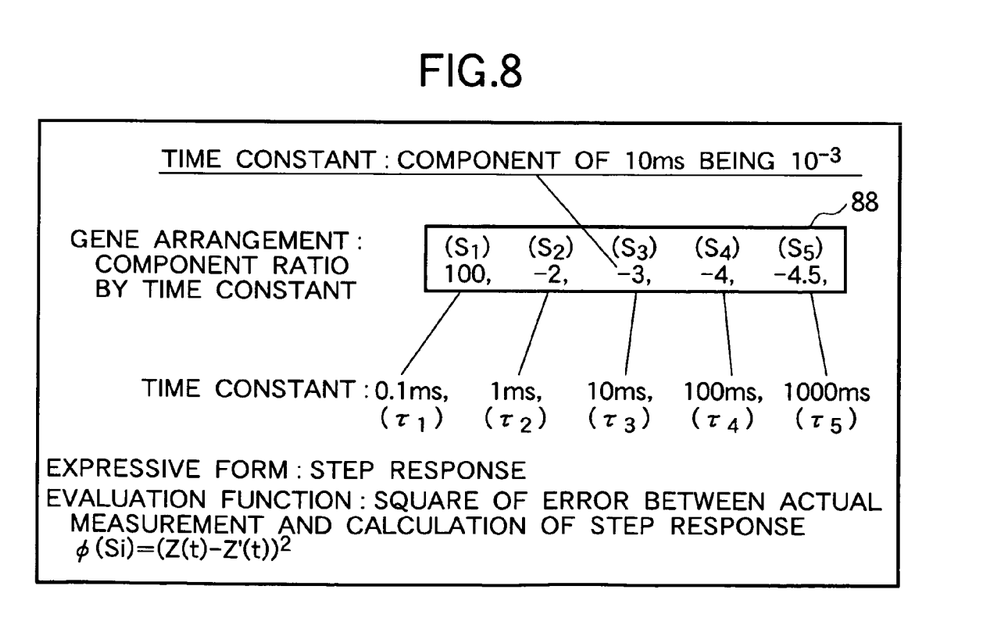
FIG. 8 is an explanatory diagram of a gene arrangement in the genetic algorithm described in FIG. 7.

A gene arrangement Sim, shown in FIG. 7, uses the component ratio Si for the time constants as the gene arrangement as shown in FIG. 8. The square error φ(Si) between the calculation Z'(t) of the step response calculated by the impulse response X(t) and the actual measurement Z(t) of the step response obtained as basic data (equation (2)) is set as the evaluation function (Equation (3)).

Further, the gene arrangement, the component ratio of the time constant, having the evaluation function φ(Si) improved in the generation alternating loop of the gene algorithm shown in FIG. 7, or is calculated asymptotically. In the genetic algorithm, a plurality of gene arrangements {Si1, Si2, Si3, . . . Sim} are used.

As shown in FIG. 7, the gene arrangements Si1 to Sim (m=10) are set at random as the initial state (Step 82). Of the generation alternating loop, for the expressive form, the calculation Z'(t) of the step response is calculated for every gene arrangement by the equation (2), described in FIG. 3 (Step 83).

The calculations are sorted by error evaluation in ascending order of the sum of the squares of the error between the actual measurement Z(t) of the step response and the calculation Z'(t) of the step response, wherein when the evaluation function φ(Si) is larger than the threshold (=2), the process shifts to step 85 (Step 84). In this error evaluation, of the evaluation functions φ(Si1), φ(Si2), . . . φ(Si10) for the impulse response X(t), a gene arrangement with the higher evaluation function is increased in the probability of surviving to the next generation, thus more preferable gene arrangements are selected.

The low-order half gene arrangements of the gene arrangements Si1 to Si10 are killed depending on the degree of the error and the upper-order half gene arrangements are increased to double by a selecting operation. Thus, poor gene arrangements are deleted and preferable gene arrangements are left (Step 85).

Part of the arrangements is exchanged with other gene arrangements in descending order of preference of the evaluation function by a crossing-over operation (Step 86). Mutation is generated in part of the gene arrangements by a mutating operation (Step 87). The generation alternating loop is repeated to asymptotically decrease the evaluation function φ(Si).

As a result of the error evaluation in the generation alternating loop, when the evaluation function φ(Si) becomes smaller than the threshold (=2), the process gets out of the generation alternating loop (Step 84), thus providing a gene arrangement 81 with a minimum error.

Figure 9:
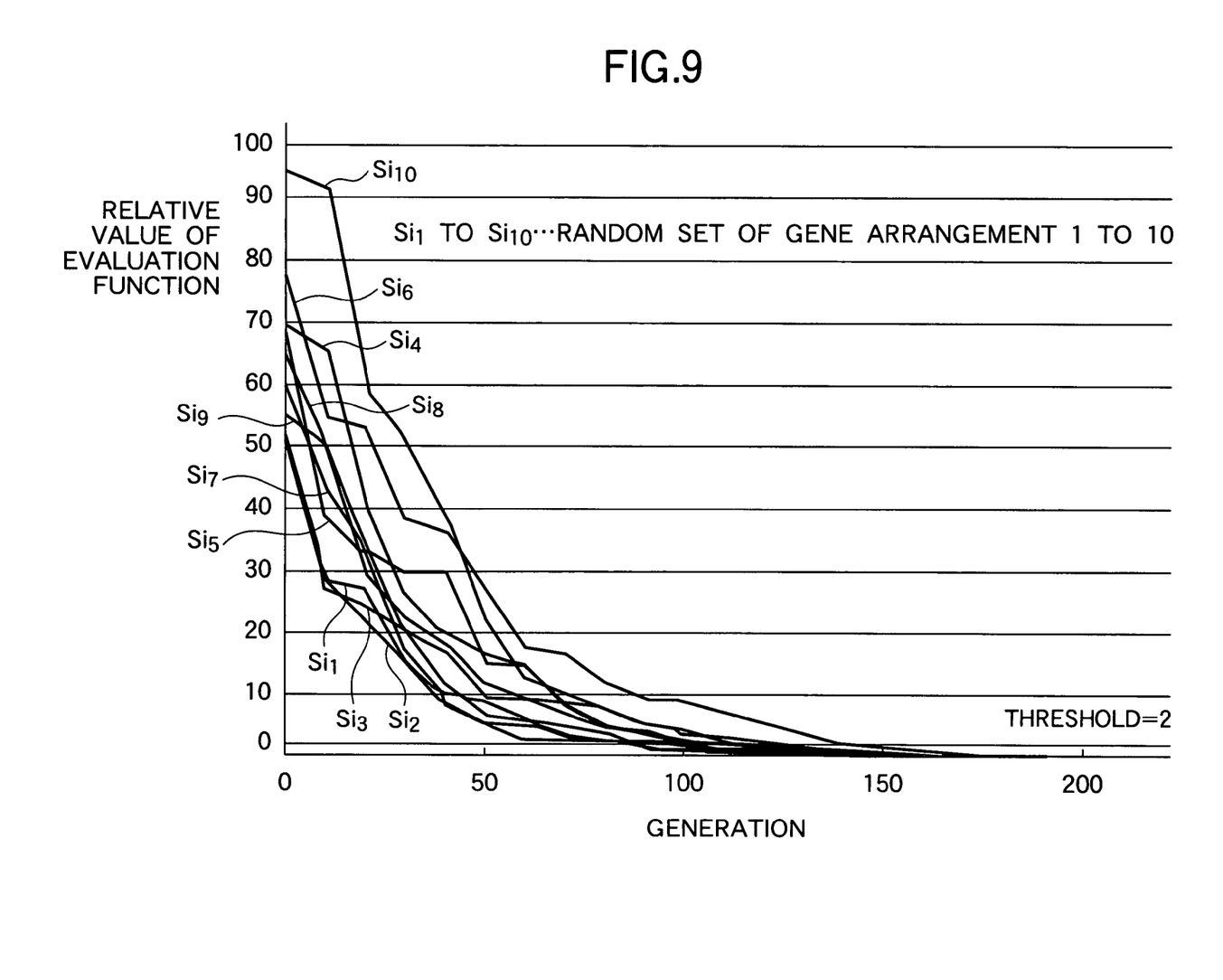
FIG. 9 is an explanatory diagram for showing change of an evaluation function in FIG. 7.

In the embodiment of the invention shown in FIG. 7, the calculation of the evaluation functions φ(Si) of the gene arrangements Si1 to Si10 for the time constant 0.1 ms for every generation alternating loop leads the result in FIG. 9. As shown in FIG. 9, in the case of the embodiment of FIG. 7, the evaluation functions φ(Si) of all the gene arrangements Si1 to Si10 become smaller than the set threshold (=2) in the 150th generation of the generation alternating loop, thus, a gene arrangement with a minimum error is obtained.

Of course, in general, the evaluation function φ(Si) cannot necessarily be made zero; however, by setting the threshold so that the evaluation function φ(Si) becomes sufficiently small in practice and by getting the process out of the generation alternating loop, the distribution 70 of the component ratios Si for time constants that represents the step response 66 in FIG. 3 can be determined.

According to the embodiment of FIGS. 7 to 9, by using the component ratios for the time constants as gene arrangements and calculating gene arrangements with a decreased error, i.e., the component ratios for the time constants asymptotically and recursively to calculate the impulse response 68 automatically with the generation alternating loop by a genetic algorithm, a high-quality X-ray CT apparatus can be achieved which has no image noise caused by an after-image due to afterglow or the like and no reduction in time resolution.

As described above, according to the embodiment, the same advantages as those of the above-described first embodiment are demonstrated. In addition thereto, there are effects of accelerating the convergence of the recursive operation and thus providing accurate component ratios at an early stage because it uses a genetic algorithm in obtaining component ratios for time constants by a recursive operation.

The X-ray tube used in the X-ray CT apparatus according to the invention is merely an embodiment of an X-ray source and is not limited thereto, and it is clear that, electronic-beam sources, radiation sources (radioisotope) and so on may be used to obtain similar effects.

The acquisition of the basic data and the calculation of the component ratios of time constants, described above, may be performed during the operation of the X-ray CT apparatus to cope with environments such as temperature in which the X-ray detector is used and the aged deterioration of the X-ray detector. For example, they may be performed during so-called air calibration done immediately before every acquisition of the image of an object. Further, they may be performed at a stage of factory shipment of the X-ray CT apparatus in order to cope with the variations in the characteristics of the X-ray detectors.

According to the embodiments, the component ratio of the time constants is calculated with respect to all the channels of the X-ray CT apparatus. However, when the X-ray detector has a plurality of modules including an X-ray detecting section in correspondence with the plurality of channels, the calculation of the component ratio may be performed only for a part of the channels of each module and the correction of the channels in a common module may be performed using a common component ratio. In other words, because X-ray detectors in an identical module formed of the same elements have a similar response characteristic, the time required for calculating the component ratio of the time constants is reduced, the capacity of a memory for memorizing the component ratios can also be reduced. Also in this case, although the calculation of corrected projection data during object radiography is performed at every individual channel, the recursive filter operations for the individual channel are the same.

The invention claimed is:
1. An X-ray CT apparatus comprising:
an X-ray source for applying X-rays to an object;
an X-ray detector arranged to face the X-ray source for detecting the amount of transmitted X-rays of the object as projection data;
basic-data acquisition means for acquiring response data of the projection data as basic data with no object in advance every time the image of the object is acquired;
analyzing means for analyzing an afterglow component of the acquired basic data into a plurality of time constants and component ratios of the afterglow component corresponding to the time constants;

storage means for storing the analyzed time constants and component ratios;

correcting means for extracting an afterglow component of the projection data on the basis of the stored time constants and components ratios during radiography of the object and removing the extracted afterglow component of the projection data from the projection data to produce corrected projection data;

reconstructing means for reconstructing an image using the produced corrected projection data; and display means for displaying the reconstructed image.

2. An X-ray CT apparatus according to claim 1, wherein the storage means stores the time constants and the component ratios of the previously acquired corrected projection data and uses them when acquiring new corrected projection data sequentially.

3. An X-ray CT apparatus comprising: an X-ray source for applying X-rays to an object; an X-ray detector arranged to face the X-ray source for determining the amount of transmitted X-rays of the object as projection data; actual-measurement acquisition means for acquiring the projection data of a step response as an actual measurement when continuous X-rays are irradiated to the X-ray detector with no object present and thereafter the irradiation is stopped; analyzing means for analyzing the step response of the acquired actual measurement into an impulse response, representing the calculation of the step response through the convolution integration of the analyzed impulse response, and calculating a plurality of time constants and their component ratios asymptotically and recursively that make the error between the actual measurement and the calculation lower than a set value; storage means for storing the calculated time constants and component ratios; correcting means for removing an afterglow component of the stored projection data from the projection data to produce corrected projection data during radiography of the object; reconstructing means for reconstructing an image using the produced corrected projection data; and display means for displaying the reconstructed image.

4. An X-ray CT apparatus comprising: an X-ray source for applying X-rays to an object; an X-ray detector arranged to face the X-ray source for determining the amount of transmitted X-rays of the object as projection data; basic-data acquisition means for acquiring response data of the projection data as basic data with no object in advance; analyzing means for analyzing an afterglow component of the acquired basic data into a plurality of time constants and their component ratios by using a genetic algorithm; storage means for storing the analyzed time constants and component ratios; correcting means for extracting an afterglow component of the projection data on the basis of the stored time constants and component ratios during radiography of the object and removing the extracted afterglow component of the projection data from the projection data to produce corrected projection data; reconstructing means for reconstructing an image using the produced corrected projection data; and display means for displaying the reconstructed image.

5. An X-ray CT apparatus according to claim 4, wherein the analyzing means calculates gene arrangements having an evaluation function improved through a generation alternating loop by the genetic algorithm asymptotically and recursively, with the component ratios for the time constants as the gene arrangements and with the error between a step response represented on the basis of an impulse response as a result of a calculation and the step response acquired as the basic data as the evaluation function, to determine the time constants and their component ratios.

6. An X-ray CT apparatus according to claim 1, wherein the X-ray detector comprises a plurality of modules having an X-ray detecting section corresponding to a plurality of channels, and the time constants and the component ratios are determined for part of the channels representing the modules.

7. An X-ray CT apparatus according to claim 1, wherein the time components and the component ratios are determined for each of the plurality of the cannels of the X-ray detector.

8. A method for correcting afterglow of an X-ray CT apparatus having an X-ray source for applying X-rays to an object and an X-ray detector arranged to face the X-ray source for determining the amount of transmitted X-rays of the object as projection data, comprising:

a basic-data acquisition step of acquiring response data of the projection data as basic data with no object present in advance every time the image of the object is acquired;

an analyzing step of analyzing an afterglow component of the acquired basic data into a plurality of time constants and component ratios of the afterglow component corresponding to the time constants;

a storing step of storing the analyzed time constants and component ratios;

a correcting step of extracting an afterglow component of the projection data on the basis of the stored time constants and component ratios during radiography of the object and removing the extracted afterglow component of the projection data from the projection data to produce corrected projection data;

a reconstructing step of reconstructing an image using the produced corrected projection data and a displaying step of displaying the reconstructed image.

9. A method for correcting afterglow of an X-ray CT apparatus according to claim 8, wherein the storing step comprises the process of storing the time constants and the component ratios of the previously acquired corrected projection data and using them when acquiring new corrected projection data sequentially.

10. A method for correcting afterglow of an X-ray CT apparatus having an X-ray source for applying X-rays to an object and an X-ray detector arranged to face the X-ray source for determining the amount of transmitted X-rays of the object as projection data, comprising:

an actual-measurement acquisition step of acquiring the projection data of a step response, as an actual measurement, when continuous X-rays are irradiated to the X-ray detector with no object present and thereafter the irradiation is stopped;

an analyzing step of analyzing the step response of the acquired actual measurement into an impulse response, representing the calculation of the step response through the convolution integration of the analyzed impulse response, and calculating a plurality of time constants and their component ratios asymptotically and recursively that make the error between the actual measurement and the calculation lower than a set value:

a storing step of storing the calculated time constants and component ratios;

a correcting step of removing an afterglow component of the stored projection data from the projection data to produce corrected projection data during radiography of the object;

a reconstructing step of reconstructing an image using the produced corrected projection data; and a displaying step of displaying the reconstructed image.

11. A method for correcting afterglow of an X-ray CT apparatus having an X-ray source for applying X-rays to an object and an X-ray detector arranged to face the X-ray source for determining the amount of transmitted X-rays of the object as projection data, comprising:

a basic-data acquisition step of acquiring response data of the projection data as basic data with no object present in advance;

an analyzing step of analyzing an afterglow component of the acquired basic data into a plurality of time constants and their component ratios by using a genetic algorithm;

a storing step of storing the analyzed time constants and component ratios;

a correcting step of extracting an afterglow component of the projection data on the basis of the stored time constants and component ratios during radiography of the object and removing the extracted afterglow component of the projection data from the projection data to produce corrected projection data;

a reconstructing step of reconstructing an image using the produced corrected projection data; and a displaying step of displaying the reconstructed image.

12. A method for correcting afterglow of an X-ray CT apparatus according to claim 11, wherein the analyzing step comprising the process of calculating gene arrangements having an evaluation function improved through a generation alternating loop by the genetic algorithm asymptotically and recursively, with the component ratios for the time constants as the gene arrangements and with the error between a step response represented on the basis of an impulse response as a result of a calculation and the step response acquired as the basic data as the evaluation function, to determine the time constants and their component ratios.

13. A program for correcting afterglow of an X-ray CT apparatus having an X-ray source for applying X-rays to an object and an X-ray detector arranged to face the X-ray source for determining the amount of transmitted X-rays of the object as projection data, comprising:

a basic-data acquisition step of acquiring response data of the projection data as basic data with no object present in advance every time the image of the object is acquired;

an analyzing step of analyzing an afterglow component of the acquired basic data into a plurality of time constants and component ratios of the afterglow component corresponding to the time constants;

a storing step of storing the analyzed time constants and component ratios;

a correcting step of extracting an afterglow component of the projection data on the basis of the stored time constants and component ratios during radiography of the object and removing the extracted afterglow component of the projection data from the projection data to produce corrected projection data;

a reconstructing step of reconstructing an image using the produced corrected projection data; and a displaying step of displaying the reconstructed image.

14. A program for correcting afterglow of an X-ray CT apparatus according to claim 13, wherein the storing step comprises the process of storing the time constants and the component ratios of the previously acquired corrected projection data and using them when acquiring new corrected projection data sequentially.

15. A program for correcting afterglow of an X-ray CT apparatus having an X-ray source for applying X-rays to an object and an X-ray detector arranged to face the X-ray source for determining the amount of transmitted X-rays of the object as projection data, comprising:

an actual-measurement acquisition step of acquiring the projection data of a step response, as an actual measurement, when continuous X-rays are applied to the X-ray detector with no object present and thereafter the application is stopped;

an analyzing step of analyzing the step response of the acquired actual measurement into an impulse response, representing the calculation of the step response through the convolution integration of the analyzed impulse response, and calculating a plurality of time constants and their component ratios asymptotically and recursively that make the error between the actual measurement and the calculation lower than a set value;

a storing step of storing the calculated time constants and component ratios; a correcting step of removing an afterglow component of the stored projection data from the projection data to produce corrected projection data during radiography of the object;

a reconstructing step of reconstructing an image using the produced corrected projection data; and a displaying step of displaying the reconstructed image.

16. A program for correcting afterglow of an X-ray CT apparatus having an X-ray source for applying X-rays to an object and an X-ray detector arranged to face the X-ray source for determining the amount of transmitted X-rays of the object as projection data, comprising:

a basic-data acquisition step of acquiring response data of the projection data as basic data with no object present in advance;

an analyzing step of analyzing an afterglow component of the acquired basic data into a plurality of time constants and their component ratios by using a genetic algorithm; a storing step of storing the analyzed time constants and component ratios;

a correcting step of extracting an afterglow component of the projection data on the basis of the stored time constants and component ratios during radiography of the object and removing the extracted afterglow component of the projection data from the projection data to produce corrected projection data;

a reconstructing step of reconstructing an image using the produced corrected projection data; and a displaying step of displaying the reconstructed image.

17. A program for correcting afterglow of an X-ray CT apparatus according to claim 16, wherein the analyzing step comprising the process of calculating gene arrangements having an evaluation function improved through a generation alternating loop by the genetic algorithm asymptotically and recursively, with the component ratios for the time constants as the gene arrangements and with the error between a step response represented on the basis of an impulse response as a result of a calculation and the step response acquired as the basic data as the evaluation function, to determine the time constants and their component ratios.

* * * * *